(12) United States Patent
Pfluecker et al.

(10) Patent No.: US 7,345,090 B2
(45) Date of Patent: Mar. 18, 2008

(54) GALENICAL FORMULATION

(75) Inventors: Frank Pfluecker, Darmstadt (DE); Joachim Buenger, Gross-Umstadt (DE); Hans-Juergen Driller, Gross-Umstadt (DE); Herwig Buchholz, Frankfurt (DE); Ralf Rosskopf, Muenster (DE)

(73) Assignee: Merck Patent Gesellschaft mit Beschraenkter Haftung, Darmstadt (DE)

( * ) Notice: Subject to any disclaimer, the term of this patent is extended or adjusted under 35 U.S.C. 154(b) by 142 days.

(21) Appl. No.: 10/833,137

(22) Filed: Apr. 28, 2004

(65) Prior Publication Data

US 2004/0202624 A1    Oct. 14, 2004

Related U.S. Application Data

(63) Continuation of application No. 09/987,439, filed on Nov. 14, 2001, now abandoned.

(30) Foreign Application Priority Data

Nov. 14, 2000 (DE) ................. 100 56 400

(51) Int. Cl.
*C07D 311/18*    (2006.01)
*A61K 31/352*    (2006.01)

(52) U.S. Cl. .............. 514/456; 549/400; 549/401; 549/403; 544/353; 548/305.1; 548/305.4; 514/249; 514/393

(58) Field of Classification Search .......... 549/400, 549/401, 403; 514/456
See application file for complete search history.

(56) References Cited

U.S. PATENT DOCUMENTS

| | | | |
|---|---|---|---|
| 5,665,367 A | 9/1997 | Burger | |
| 5,718,906 A | 2/1998 | Martin | |
| 5,952,373 A | 9/1999 | Lanzendorfer | |
| 6,121,243 A | 9/2000 | Lanzendorfer | |
| 6,180,662 B1 | 1/2001 | Lanzendorfer | |

FOREIGN PATENT DOCUMENTS

| | | |
|---|---|---|
| DE | 19 508 608 | 9/1995 |
| EP | 0 716 847 | 11/1995 |
| FR | 2 687 572 | 2/1992 |
| FR | 2 687 572 | 8/1993 |
| FR | 2 708 851 | 2/1995 |

OTHER PUBLICATIONS

Samejima et al., CAPLUS Abstract 130:65484, 1998.*
Joon-Su Shin, et al., "Synthesis and Hypoglycemic Effect of Chrysin Derivatives", Bioorganic & Medicinal Chemistry Letters 9, (1999), pp. 869-874.
Kim et al., CAPLUS Abstract 132:251003, 1999.
Shin et al., CAPLUS Abstract 131:58671, 1999.
English Abstract of FR 2687572, 1992.
English Abstract of FR 2708851, 1995.

* cited by examiner

*Primary Examiner*—Deepak Rao
(74) *Attorney, Agent, or Firm*—Millen, White, Zelano, Branigan, P.C.

(57) ABSTRACT

The invention relates to compounds of the formula I

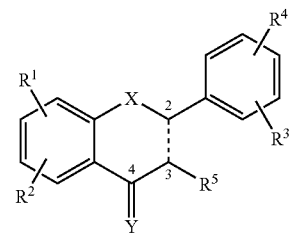

where $R^1$, $R^2$, $R^3$, $R^4$ and $R^5$ have the meanings given in claim 1. The compound is suitable in particular for use in skin care compositions. They protect, firstly, against harmful oxidation reactions and, secondly, also act as UV filters.

28 Claims, No Drawings

GALENICAL FORMULATION

This application is a continuation of U.S. application Ser. No. 09/987,439, filed Nov. 14, 2001, now abandoned, which claimed priority of DE 100 56 400.3, filed Nov. 14, 2000.

The invention relates to compounds of the formula I

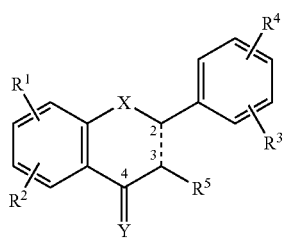

where X, Y, $R^1$, $R^2$, $R^3$, $R^4$ and $R^5$ have the meanings defined herein.

A suntan of the skin to whatever degree is regarded in today's society as attractive and as an expression of vigour and sportiness. As well as this desired effect of the sun on the skin, a number of undesired secondary effects arise, such as sunburn or premature skin ageing and the formation of wrinkles. In the meantime, a number of performance UV filters have been developed which, applied to the skin in the form of creams, lotions or gels, can effectively delay the development of sunburn even when the incidence of solar rays is relatively high. The UV filter present in the pharmaceutical or cosmetic preparation forms a film or a layer on the surface of the skin and does not penetrate into deeper skin layers with other care substances present in the preparation. Known UV filters or sun protection agents thus act only by absorbing certain regions of sunlight, meaning that this radiation cannot penetrate into deeper layers of the skin. As is known, the most hazardous part of solar radiation is formed by the ultraviolet rays having a wavelength of less than 400 nm. The lower limit of the ultraviolet rays which reach the surface of the earth is limited by the absorption in the ozone layer to about 280 nm. The sun protection filters which are nowadays customary in cosmetics absorb in a wavelength range from 280 to 400 nm. This range includes UV-B rays having a wavelength between 280 and 320 nm, which play a decisive role in the formation of a solar erythema, and also UV-A rays, having a wavelength between 320 and 400 nm, which tan the skin but also age it, favour the triggering of an erythematous reaction or can exacerbate this reaction in certain people or even trigger phototoxic or photoallergic and irritative reactions.

Skin damage is caused not only by sunlight, but also by other external influences, such as cold or warmth. In addition the skin is subject to natural ageing, as a result of which wrinkles appear and the elasticity of the skin decreases.

The object of care cosmetics is, wherever possible, to obtain the impression of a youthful skin. In principle, there are various ways of achieving this object. For example, existing skin damage, such as irregular pigmentation or the formation of wrinkles can be smoothed out by concealing powders or creams. Another approach is to protect the skin against environmental influences which lead to permanent damage and thus ageing of the skin. The idea is therefore to intervene in a preventative manner and thus to delay the ageing process. One example of this is the UV filters already mentioned which, by absorbing certain wavelength regions, prevent or at least reduce skin damage. While in the case of UV filters, the harmful phenomenon, the UV radiation, is screened from the skin, in another way, attempts have been made to support the natural defence or repair mechanisms of the skin against the harmful phenomenon. Finally, another approach involves compensating for the defence functions of the skin toward harmful influences, which weaken with increasing age, by externally applying substances which are able to compensate for this diminishing defence or repair function. For example, the skin has the ability to scavenge free radicals which are produced by external or internal stress factors. This ability decreases with increasing age, as a result of which the ageing process accelerates with increasing age.

Substances which are to support or compensate for defence and repair functions in the skin must be able to be transported to their site of activity. In principle, there are two ways of achieving this. Either the substance is applied to the skin and penetrates through the external layers into the deeper layers of the skin, or the active ingredient is, for example, following oral administration, transported via the bloodstream to the site of activity.

A further difficulty associated with the preparation of cosmetics is the fact that active ingredients which are to be incorporated into cosmetic formulations are often unstable and may become damaged in the formulation. The damage can be caused, for example, as a result of a reaction with atmospheric oxygen or as a result of the absorption of UV rays. The molecules damaged in this way can, as a result of a change in their structure, for example, change their colour and/or lose their effectiveness.

DE 195 08 608 describes an unstable cosmetic composition for protection against UV rays of wavelength between 280 and 400 nm which comprises at least one tetraalkylquercetin in a cosmetically acceptable oil-based medium, and novel tetraalkylquercetins.

FR 2 687 572 describes the use of flavonoids which do not have a double bond at position 2, 3 or do not simultaneously have a double bond at position 2, 3 and a hydroxyl group at position 3, for the preparation of cosmetic compositions, and as active ingredients for protecting the skin, the hair or cosmetic compositions against singlet oxygen.

EP 0 716 847 A1 describes a cosmetic or dermatological active ingredient combination of cinnamic acid derivatives and flavone glycosides. The active ingredient combination here acts as an antioxidant. It is suitable for the combating or the prophylaxis of skin ageing. The active ingredient combination may also comprise UV filter substances as a further constituent.

U.S. Pat. No. 5,665,367 describes a skincare composition which comprises retinol or a retinyl ester and a flavonoid chosen from the group consisting of naringenin and quercetin, which comprises a suitable cosmetic carrier. The composition can also comprise UV filters as a further component.

FR 2 708 851 describes a cosmetic composition which comprises nanopigments and, as antioxidants, flavonoids. A further ingredient which may be present is also UV-A or UV-B filters.

An object of the invention is to provide compounds which both act as antioxidants and also are able to effect protection against UV radiation.

Upon further study of the specification and appended claims, further objects and advantages of this invention will become apparent to those skilled in the art.

These objects are achieved by compounds of the formula I

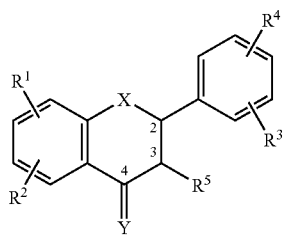

where

X is O, S or NH;

Y is O, S or NH a single or a double bond may be provided between carbon atoms C-2 and C-3, where $R^1$, $R^2$, $R^3$, $R^4$ and $R^5$ may be identical or different and, independently of one another are —H, —OH or -OA, and A is a group which absorbs UV radiation, preferably in the UV-A and/or UV-B region, which is chosen from the group formed from

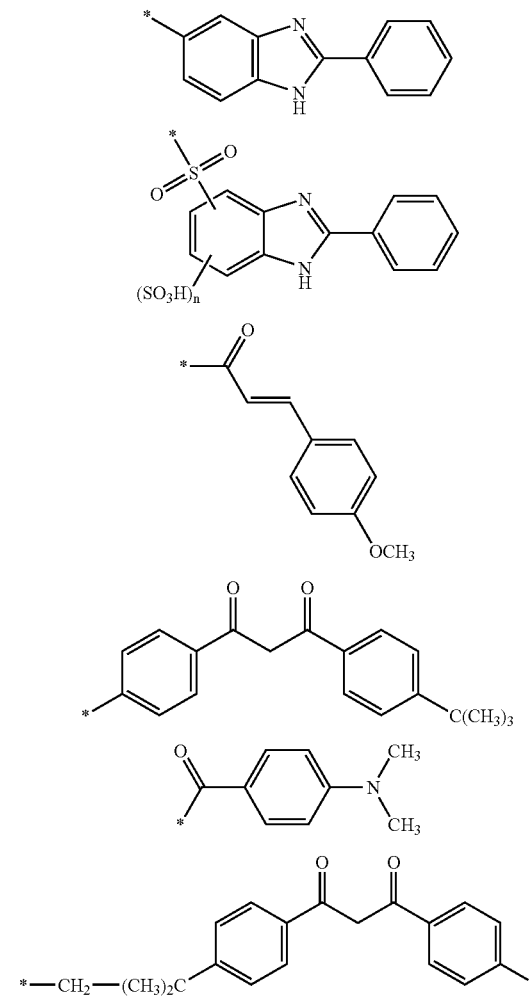

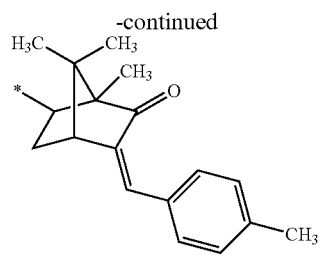

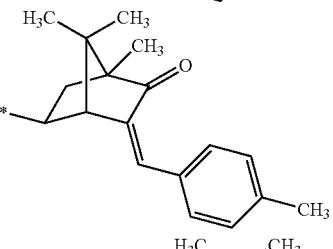

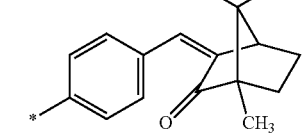

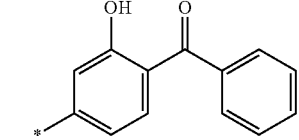

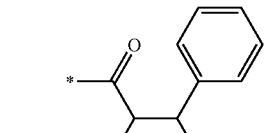

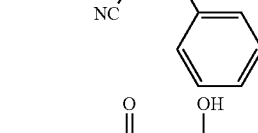

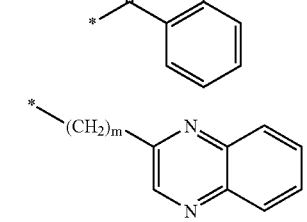

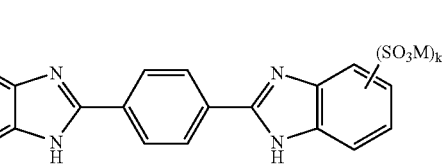

where n=, 1, 2 or 3 m=0 or 1 k=0, 1, 2, 3 or 4

M=H, Na or K and at least one of the groups $R^1$, $R^2$, $R^3$, $R^4$ or $R^5$ is formed by -OA.

The compounds preferably have a structure of the formula II

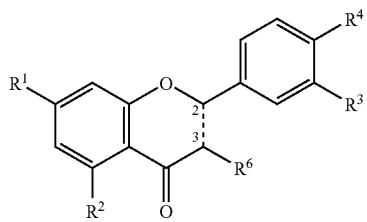

where $R^1$, $R^2$, $R^3$, $R^4$ and $R^5$ have the meanings given above and below.

The flavonoids which form the base substance of the compounds of the formula I have activity as antioxidants and/or free-radical scavengers. Their combination with groups which exhibit a suitable absorption in the UV region provides a new class of compound which has very interesting properties.

As well as their action as antioxidant, the flavonoids used as base substances themselves exhibit a certain protective action against UVA radiation. Therefore, by combining them with UV-absorbing groups, it is possible to provide UVA/B broad-band filters which also have an antioxidative effect. In this connection, the groups are chosen such that they exhibit an absorption maximum in particular in the wavelength ranges of UVA and of UVB radiation which are particularly harmful for the skin. The UVB portion of sunlight covers the range from 280 to 320 nm, and the UVA radiation the range >320 nm, which directly borders the visible light region. UV broad-band filters of this type can be used, for example, in a large number of cosmetics.

As a result of their antioxidative effect, compounds of the formula I also have a stabilizing action on formulations which are used for cosmetics. By adding compounds of the formula I to the corresponding products, the latter thus remain stable for longer and do not change their appearance. In particular, in cases of longer-lasting application or prolonged storage, the effectiveness of the ingredients, e.g. vitamins, is also retained. This is particularly advantageous in the case of sunscreen compositions since these cosmetics are subjected to particularly high stresses by UV rays.

The substances of the formula I generally act as free-radical scavengers. Such free radicals are produced not only as a result of sunlight, but are formed under a variety of conditions. Examples are anoxia which block the electron flow upstream of the cytochrome oxidases and bring about the formation of superoxide radical anions; inflammations which are associated inter alia with the formation of superoxide anions as a result of membrane NADPH oxidase of leukocytes which, however, are also associated with the formation (as a result of disproportionation in the presence of iron(II) ions) of hydroxyl radicals and other reactive species normally involved in the phenomenon of phagocytosis; and lipid autoxidation which is generally initiated by a hydroxyl radical and produces lipidic alkoxy radicals and hydroperoxides.

The compounds of the formula I also act as enzyme inhibitors. For example, they inhibit histidine decarboxylase, protein kinases, elastase, aldose reductase and hyaluronidase, which would make it possible to maintain the entirety of the base substance of vascular sheaths. In addition, they do not specifically inhibit catechol O-methyltransferase, as a result of which the amount of available catecholamines and, consequently, vascular strength can be increased. As a further effect, they inhibit AMP phosphodiesterase, as a result of which the substances may have potential for inhibiting platelet aggregation.

These properties permit, for example, a use of compounds of the formula I for a large number of therapeutic applications. They are, for example, suitable for protecting DNA. Further uses arise from their effect as an antiviral agent, in particular as an agent against herpes. In addition, they can be used as bacteriostatic or bactericidal agents or else as antiinflammatory agents.

Compounds of the formula I are in most cases not used without a diluent, but are incorporated into suitable formulations, such as creams, ointments or lotions. The compounds can be used by application to the skin, but systemic transportation is also conceivable. For this purpose, the properties of the compounds of the formula I have to be matched to the conditions in question. Modification of the solubility in oil or water is possible by introducing corresponding groups into the molecule. Compounds which have been found to be suitable are those where in addition $R^1$, $R^2$, $R^3$, $R^4$ and $R^5$, independently of one another, have the meanings of —H, —OH, -OA, with A having the meaning given above, or one of the following meanings:

straight-chain or branched oxalkyl or carboxyalkyl group having 1 to 12 carbon atoms, straight-chain or branched oxalkenyl or carboxyalkenyl group having 2 to 12 carbon atoms, straight-chain or branched hydroxyoxalkyl group having 1 to 12 carbon atoms, where the hydroxyl group may be bonded to a primary or secondary carbon atom and, furthermore, the alkyl chain may also be interrupted by oxygen, sulphate group, phosphate group and a mono- or oligoglycosyl radical, where these groups may be substituted by alkyl, hydroxyl, alkoxy, amino, mono- and dialkylamino, sulphonic acid, carboxyl and/or halogen groups, and wherein at least one of the groups is an -OA group.

To improve the solubility in oil, the hydroxyl groups of the flavonoid base substance are etherified with suitable alcohols. A particularly suitable alkyl group is the 2-ethylhexyl group.

The solubility in oil can also be improved by, for example, esterifying the hydroxyl groups of the flavonoid base substance with 2-ethylhexanecarboxylic acid.

Further suitable radicals are obtained by esterification with monocarboxylic acids, such as butyric acid, valeric acid, hexanoic acid, sorbic acid, ascorbic acid or lauric acid. These radicals promote the transportation of the compound through biological membranes. In the cell, the base substance can then be liberated by cleaving off the carboxylic acids using esterases.

The solubility in water can be improved by introducing sulphate or phosphate groups into the molecule. Suitable for this are either compounds with one, two or three sulphate groups in the molecule, or mixtures of different sulphates or phosphates.

Preference is also given to choosing those structures in which at least one of the radicals $R^1$, $R^2$, $R^3$, $R^4$. and $R^5$ is formed by a mono- or oligosaccharide. Preference is given here to hexosyl radicals, in particular rhamnosyl radicals and glucosyl radicals. However, other hexosyl radicals, for example allosyl, altrosyl, galactosyl, gulosyl, idosyl, mannosyl and talosyl, can also be used advantageously in some instances. It may also be advantageous to use pentosyl radicals. The glucosyl radicals can be bonded to the base substance by means of α- or β-glycoside bonds. A preferred disaccharide is, for example, 6-O-(6-deoxy-α-L-mannopyranosyl)-β-D-glucopyranoside.

The compounds of the formula I are prepared by methods known per se to the person skilled in the art and are described in standard works such as Houben-Weyl, "Methoden der organischen Chemie" [Methods of Organic Chemistry], Georg-Thieme-Verlag, Stuttgart.

The radicals can be introduced, for example, starting from the known flavonoid base substances. Thus, alkyl chains can be introduced by reacting the base substance with the corresponding alkyl halides under the action of a strong base in a suitable solvent, for example dimethylformamide. If the radicals $R^1$ to $R^5$ bind as esters, this can be carried out, for example, by reaction with a corresponding acid chloride. Scheme 1 shows examples of a few precursors of radicals which are suitable for introduction of the radicals in the respective base substance. Here, —X is a suitable leaving group, for example a halide. This list is only given by way of example and shows only a small fraction of the number of possible precursors. It is directly possible for the person skilled in the art to assign other suitable leaving groups, for example a tosylate group or a triflate group, instead of the halides. For example, introduction of the radicals bonded via an ester function is also possible via corresponding transesterification reactions.

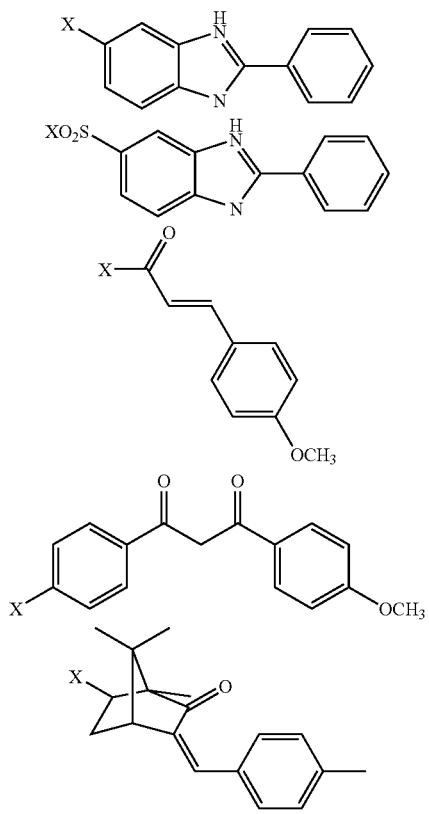

Scheme 1: Examples of Suitable Precursors for Introducing Radicals $R^1$, $R^2$, $R^3$, $R^4$ and $R^5$ The compounds of the formula I can either be used as pure compounds, or it is also possible to use mixtures, this term here being understood as meaning both isomeric mixtures and also mixtures of compounds of the formula I which have different substitution patterns, i.e. carry, for example, a different number of substituents -OA.

The reaction of the flavonoid base substances with the corresponding reactive precursors of the radicals $R^1$ to $R^5$ is carried out by methods known to the person skilled in the art and in customary solvents. Suitable solvents are, for example, chlorinated hydrocarbons, dimethyl sulphoxide, dimethylformamide etc.

The compounds of the formula I may display an advantageous effect on the skin. The invention thus also provides a cosmetic or pharmaceutical formulation comprising at least one compound of the formula I.

The positive effect of the cosmetic or pharmaceutical preparation according to the invention is presumably based on the effect of the compounds of the formula I as antioxidants or free-radical scavengers in combination with an action as UV filters. In order to be able to develop their positive effect on the skin, the compounds of the formula I should be able to penetrate into deeper layers of the skin. For this, a number of possibilities are available. Firstly, the compounds of the formula I can have sufficient lipophilicity in order to be able to penetrate through the outer layer of the skin into epidermal layers. Another possibility involves also providing corresponding transportation agents, for example liposomes, which permit transportation of the compounds of the formula I through the external layers of skin, in the preparation. Finally, a systemic transportation of the compounds of the formula I is also conceivable. The preparation is then formulated, for example, such that it is suitable for oral administration.

The one or more compounds of the formula I can be incorporated into cosmetic formulations in the customary manner. For internal use, administration forms such as capsules, sugar-coated tablets, powders, tablet solutions or solutions are suitable.

Examples which may be mentioned of administration forms of the cosmetic or pharmaceutical formulations according to the invention for external use are: solutions, suspensions, emulsions, PIT emulsions, pastes, ointments, gels, creams, lotions, powders, soaps, surfactant-containing cleansing preparations, oils, aerosols and sprays. Further application forms are, for example, sticks, shampoos and shower preparations. Customary carriers, auxiliaries and optionally further active ingredients may be added to the formulation.

Preferred auxiliaries originate from the group of preservatives, antioxidants, stabilizers, solubility promoters, vitamins, colorants, odour improvers.

Ointments, pastes, creams and gels may comprise the customary carriers, e.g. animal and vegetable fats, waxes, paraffins, starch, tragacanth, cellulose derivatives, polyethylene glycols, silicones, bentonites, silica, talc and zinc oxide or mixtures of these substances.

Powders and sprays may comprise the customary carriers, e.g. lactose, talc, silica, aluminium hydroxide, calcium silicate and polyamide powder or mixtures of these substances. Sprays can additionally comprise customary propellants, e.g. chlorofluorocarbons, propane/butane or dimethyl ether.

Solutions and emulsions can comprise the customary carriers, such as solvents, solubility promoters and emulsifiers, e.g. water, ethanol, isopropanol, ethyl carbonate, ethyl acetate, benzyl alcohol, benzyl benzoate, propylene glycol, 1,3-butyl glycol, oils, in particular cottonseed oil, peanut oil, maize germ oil, olive oil, castor oil and sesame oil, glycerol fatty acid esters, polyethylene glycols and fatty acid esters of sorbitan or mixtures of these substances.

Suspensions can comprise the customary carriers such as liquid diluents, e.g. water, ethanol or propylene glycol, suspending agents, e.g. ethoxylated isostearyl alcohols, polyoxyethylene sorbitol ester and polyoxyethylene sorbitan ester, microcrystalline cellulose, aluminium metahydroxide, bentonite, agar agar and tragacanth or mixtures of these substances.

Soaps can comprise the customary carriers, such as alkali metal salts of fatty acids, salts of fatty acid monoesters, fatty acid protein hydrolysates, isethionates, lanolin, fatty alcohol, plant oils, plant extracts, glycerol, sugars or mixtures of these substances.

Surfactant-containing cleansing products can comprise the customary carrier substances, such as salts of fatty alcohol sulphates, fatty alcohol ether sulphates, sulphosuccinic monoesters, fatty acid protein hydrolysates, isethionates, imidazolinium derivatives, methyl taurates, sarcosinates, fatty acid amide ether sulphates, alkylamidobetaines, fatty alcohols, fatty acid glycerides, fatty acid diethanolamides, vegetable and synthetic oils, lanolin derivatives, ethoxylated glycerol fatty acid esters or mixtures of these substances.

Face and body oils can comprise the customary carrier substances such as synthetic oils, such as fatty acid esters, fatty alcohols, silicone oils, natural oils, such as vegetable oils and oily plant extracts, paraffin oils, lanolin oils or mixtures of these substances.

Further typically cosmetic application forms are also lipsticks, lipcare sticks, mascara, eyeliner, eyeshadow, blusher, powder make-up, emulsion make-up and wax make-up, and sunscreen, presun and aftersun preparations.

All compounds or components which can be used in the cosmetic formulations are either known and available commercially or can be synthesized by known processes.

The cosmetic preparation according to the invention is particularly suitable for protecting human skin against ageing processes and against oxidative stress, i.e. against damage caused by free radicals, as are produced, for example, by solar irradiation, heat or other influences. In this connection, they are in various administration forms customarily used for this application. For example, it may in particular be in the form of a lotion or emulsion, such as in the form of a cream or milk (O/W, W/O, O/W/O, W/O/W), in the form of oily-alcoholic, oily-aqueous or aqueous-alcoholic gels or solutions, in the form of solid sticks or may be formulated as an aerosol.

The formulation may comprise cosmetic auxiliaries which are customarily used in this type of preparation, such as, for example, thickeners, emollients, moisturizers, interface-active agents, emulsifiers, preservatives, antifoams, perfumes, waxes, lanolin, propellants, dyes and/or pigments which colour the composition itself or the skin, and other ingredients customarily used in cosmetics.

As dispersant or solubilizer it is possible to use an oil, wax or other fatty substance, a lower monoalcohol or a lower polyol or mixtures thereof. Particularly preferred monoalcohols or polyols include ethanol, isopropanol, propylene glycol, glycerol and sorbitol.

A preferred embodiment of the invention is an emulsion in the form of a protective cream or milk and which, apart from the compound(s) of the formula I, comprises, for example, fatty alcohols, fatty acids, fatty acid esters, in particular triglycerides of fatty acids, lanolin, natural and synthetic oils or waxes and emulsifiers in the presence of water.

Further preferred embodiments are oily lotions based on natural or synthetic oils and waxes, lanolin, fatty acid esters, in particular triglycerides of fatty acids, or oily-alcoholic lotions based on a lower alcohol, such as ethanol, or a glycerol, such as propylene glycol, and/or a polyol, such as glycerol, and oils, waxes and fatty acid esters, such as triglycerides of fatty acids.

The cosmetic preparation according to the invention can also be in the form of an alcoholic gel which comprises one or more lower alcohols or polyols, such as ethanol, propylene glycol or glycerol, and a thickener, such as siliceous earth. The oily-alcoholic gels also comprise natural or synthetic oil or wax.

The solid sticks consist of natural or synthetic waxes and oils, fatty alcohols, fatty acids, fatty acid esters, lanolin and other fatty substances. If a preparation is formulated as an aerosol, the customary propellants, such as alkanes, fluoroalkanes and chlorofluoroalkanes are usually used.

The cosmetic formulation can also be used to protect the hair against photochemical damage in order to prevent changes of colour shades, decoloration or damage of a mechanical nature. In this case, a suitable formulation is in the form of a shampoo, lotion, gel or emulsion for rinsing out, the formulation in question being applied before or after shampooing, before or after colouring or bleaching or before or after permanent waving. It is also possible to choose a formulation in the form of a lotion or gel for styling or treating the hair, in the form of a lotion or gel for brushing or blow-waving, in the form of a hair lacquer, permanent waving composition, colorant or bleach for the hair. Apart from the compound(s) of the formula I, the cosmetic or pharmaceutical formulation may comprise various adjuvants used in this type of composition, such as interface-active agents, thickeners, polymers, emollients, preservatives, foam stabilizers, electrolytes, organic solvents, silicone derivatives, oils, waxes, antigrease agents, dyes and/or pigments which colour the composition itself or the hair, or other ingredients customarily used for hair care.

The cosmetic preparations according to the invention can be prepared using techniques which are well known to the person skilled in the art.

To protect the skin and/or natural or sensitized hair against solar rays, a cosmetic preparation comprising one or more compounds of formula I is applied to the skin or the hair. Sensitized hair is understood here as meaning hair which has been subjected to a chemical treatment, such as a permanent waving treatment, a colouring process or bleaching process.

The protective action against UV radiation can be improved if the formulation comprises one or more UV filters.

In principle, all UV filters are suitable for a combination. Particular preference is given to those UV filters whose physiological safety has already been demonstrated. There are many tried and tested substances known from the specialist literature both for UVA and also UVB filters, e.g.

benzylidenecamphor derivatives, such as
  3-(4'-methylbenzylidene)-dl-camphor (e.g. Eusolex® 6300),
  3-benzylidenecamphor (e.g. Mexoryl® SD),
  polymers of N-{(2 and 4)-[(2-oxoborn-3-ylidene)methyl] benzyl}acrylamide (e.g. Mexoryl® SW),
  N,N,N,-trimethyl-4-(2-oxoborn-3-ylidenemethyl) anilinium methylsulphate (e.g. Mexoryl® SK) or
  α-(2-oxoborn-3-ylidene)toluene-4-sulfonic acid (e.g. Mexoryl® SL), benzoylmethanes or dibenzoylmethanes, such as
- 1-(4-tert-butylphenyl)-3-(4-methoxyphenyl)propane-1,3-dione (e.g. Eusolex® 9020) or
- 4-isopropyldibenzoylmethane, (e.g. Eusolex® 8020), benzophenones, such as
- 2-hydroxy-4-methoxybenzophenone (e.g. Eusolex® 4360) or
- 2-hydroxy-4-methoxybenzophenone-5-sulfonic acid and its sodium salt (e.g. Uvinul® MS-40), methoxycinnamic esters, such as
- octyl methoxycinnamate (e.g. Eusolex® 2292),
- isopentyl 4-methoxycinnamate, e.g. as a mixture of the isomers (e.g. Neo Heliopan® E 1000), salicylate derivatives, such as
- 2-ethylhexyl salicylate (e.g. Eusolex® OS),
- 4-isopropylbenzyl salicylate (e.g. Megasol®) or
- 3,3,5-trimethylcyclohexyl salicylate (e.g. Eusolex®D HMS), 4-aminobenzoic acid and derivatives, such as
- 4-aminobenzoic acid,
- 2-ethylhexyl 4-(dimethylamino)benzoate (e.g. Eusolex® 6007),
- ethoxylated ethyl 4-aminobenzoate (e.g. Uvinul® P25), and further substances, such as
- 2-ethylhexyl 2-cyano-3,3-diphenylacrylate (e.g. Eusolex® OCR),
- 2-phenylbenzimidazole-5-sulphonic acid, and its potassium, sodium and triethanolamine salts (e.g. Eusolex® 232),
- 3,3'-(1,4-phenylenedimethylene)-bis(7,7-dimethyl-2-oxobicyclo-[2.2.1]hept-1-ylmethanesulphonic acid and salts thereof (e.g. Mexoryl® SX) and
- 2,4,6-trianilino(p-carbo-2'-ethylhexyl-1'-oxy)-1,3,5-triazine (e.g. Uvinul® T 150)
- 4,4-diaryl butadienes.

The compounds given in the list are only to be regarded as examples. It is of course also possible to use other UV filters.

These organic UV filters are usually incorporated into cosmetic formulations in an amount of from 0.5 to 10% by weight, preferably 1-8%.

Examples of further suitable organic UV filters are
- 2-(2H-benzotriazol-2-yl)-4-methyl-6-(2-methyl-3-(1,3,3,3-tetramethyl-1-(trimethylsilyloxy)disiloxanyl)propyl)phenol (e.g. Silatriazole®),
- bis(2-ethylhexyl) 4,4'-[(6-[4-((1,1,-dimethylethyl)aminocarbonyl)phenylamino]-1,3,5-triazine-2,4-diyl)diimino]bis(benzoate) (e.g. Uvasorb® HEB),
- α-(trimethylsilyl)-ω-[(trimethylsilyl)oxy]poly[oxy(dimethyl [and approximately 6% methyl[2-[p-[2,2-bis(ethoxycarbonyl)vinyl]phenoxy]-1-methyleneethyl] and about 1.5% methyl[3-[p-2,2-bis(ethoxycarbonyl)vinyl)phenoxy)propenyl) and 0.1 to 0.4% (methylhydrogen)silylene]] (n≈60) (CAS No. 207 574-74-1),
- 2,2'-methylenebis(6-(2H-benzotriazol-2-yl)-4-(1,1,3,3-tetramethylbutyl)phenol) (CAS No. 103 597-45-1),
- 2,2'-(1,4-phenylene)bis(1H-benzimidazole-4,6-disulphonic acid, monosodium salt) (CAS No. 180 898-37-7) and
- 2,4-bis{[4-(2-ethylhexyloxy)-2-hydroxy]phenyl}-6-(4-methoxyphenyl)-1,3,5-triazine (CAS No. 187 393-00-6).

These organic UV filters are usually incorporated into cosmetic formulations in an amount of from 0.5 to 20% to 20% by weight, preferably 1-15%.

Conceivable inorganic UV filters are those from the group of titanium dioxides, such as, for example, coated titanium dioxide (e.g. Eusolex® T-2000, Eusolex® T-AQUA), zinc oxides (e.g. Sachtotec®), iron oxides and also cerium oxides. These inorganic UV filters are usually incorporated into cosmetic formulations in an amount of from 0.5 to 20% by weight, preferably 2-10%.

Preferred compounds with UV-filtering properties are 3-(4'-methylbenzylidene)-dl-camphor, 1-(4-tert-butylphenyl)-3-(4-methoxyphenyl)propane-1,3-dione, 4-isopropyldibenzoylmethane, 2-hydroxy-4-methoxy-benzophenone, octyl methoxy-cinnamate, 3,3,5-trimethylcyclohexyl salicylate, 2-ethylhexyl 4-(dimethylamino)-benzoate, 2-ethylhexyl 2-cyano-3,3-diphenylacrylate, 2-phenylbenzimidazole-5-sulphonic acid, and its potassium, sodium and triethanolamine salts.

The organic or inorganic UV filters can be combined as desired with the compounds of the formula I. Based on the weight, the ratio of UV filters to the compounds of the formula I is preferably chosen between 1:10 and 10:1, in particular between 1:5 and 5:1.

By combining one or more compounds of the formula I with further UV filters, the protective action against harmful effects of UV radiation can be optimized. The combination then demonstrates both a protective action as antioxidant and also against burns by UV radiation.

The protecting action against oxidative stress or against the effect of free radicals can be further improved if the formulation comprises one or more further antioxidants.

There are many tried and tested substances known from the specialist literature which can be used, e.g. amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotenoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof), and salts thereof, dilauryl thiodipropionate, distearyl thiodipropionate, thiodipropionic acid and derivatives thereof (esters, ethers, peptides, lipids, nucleotides, nucleosides and salts), and sulphoximine compounds (e.g. buthionine-sulphoximine, homocysteine-sulphoximine, buthionine-sulphones, penta-, hexa- and heptathionine-sulphoximine) in very low tolerated doses (e.g. pmol to µmol/kg), and also (metal) chelating agents, (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof, vitamin C and derivatives (e.g. ascorbyl palmitate, magnesium ascorbyl phosphate, ascorbyl acetate), tocopherols and derivatives (e.g. vitamin E acetate), vitamin A and derivatives (e.g. vitamin A palmitate), and coniferyl benzoate of benzoin resin, rutinic acid and derivatives thereof, α-glycosyl rutin, ferulic acid, furfurylideneglucitol, carnosine, butylhydroxytoluene, butylhydroxyanisole, nordihydroguaiaretic acid, trihydroxybutyrophenone, quercetin, uric acid and derivatives thereof, mannose and derivatives thereof, zinc and derivatives thereof (e.g. ZnO, ZnSO$_4$), selenium and derivatives thereof (e.g. selenomethionine), stilbenes and derivatives thereof (e.g. stilbene oxide, trans-stilbene oxide).

Mixtures of antioxidants are likewise suitable for use in the cosmetic formulations according to the invention. Known and commercial mixtures are, for example, mixtures comprising, as active ingredients, lecithin, L-(+)-ascorbyl palmitate and citric acid (e.g. Oxynex® AP), natural tocopherols, L-(+)-ascorbyl palmitate, L-(+)-ascorbic acid and citric acid (e.g. Oxynex® K LIQUID), tocopherol extracts from natural sources, L-(+)-ascorbic acid and citric acid (e.g. Oxynex® L LIQUID), DL-α-tocopherol, citric acid and lecithin (e.g. Oxynex® LM) or butylhydroxytoluene (BHT), L-(+)-ascorbyl palmitate and citric acid (e.g. Oxynex® 2004).

The antioxidants can be combined as desired with the compounds of the formula I. Based on the weight, the ratio of the antioxidant to the compounds of the formula I is preferably chosen between 1:10 and 10:1, in particular between 1:5 and 5:1.

The formulations according to the invention can comprise vitamins as further ingredients. Preferably, vitamins and vitamin derivatives chosen from vitamin A, vitamin A propionate, vitamin A palmitate, vitamin A acetate, retinol, vitamin B, thiamine chloride hydrochloride (vitamin B$_1$), riboflavin (vitamin B$_2$) nicotinamide, vitamin C (ascorbic acid), vitamin D, ergocalciferol (vitamin D$_2$), vitamin E, DL-α-tocopherol, tocopherol E acetate, tocopherol hydrogensuccinate, vitamin K$_1$, esculin (vitamin P active ingredient), thiamine (vitamin B$_1$) nicotinic acid (niacin), pyridoxine, pyridoxal, pyridoxamine, (vitamin B$_6$), pantothenic acid, biotin, folic acid and cobalamine (vitamin B$_{12}$) are present in the cosmetic formulations according to the invention, particularly preferably vitamin A palmitate, vitamin C, DL-α-tocopherol, tocopherol E acetate, nicotinic acid, pantothenic acid and biotin.

Furthermore, the formulation according to the invention may also comprise, as ingredient, ectoin (2-methyl-1,4,5,6-tetrahydropyrimidine-4-carboxylic acid) and in that case effects protection of the Langerhans cells. By adding 1-(2-hydroxyphenyl)alkan-1-one oxime, the formulation according to the invention develops an antiinflammatory action.

The cosmetic or pharmaceutical formulation comprising at least one compound of the formula I is suitable particularly for protecting the body's cells against oxidative stress, in particular for reducing skin ageing.

Also to be regarded as positive are the properties of compounds having the formula I for use in foodstuffs or as food supplements or as "functional food". The explanations below given for foodstuffs also apply analogously to food supplements and to "functional food".

The foodstuffs which can be enriched according to the present invention with one or more compounds of the formula I include all materials which are suitable for consumption by animals or for consumption by humans, for example vitamins and provitamins thereof, fats, minerals or amino acids. (The foodstuffs may be solid, or else liquid, i.e. be in the form of a drink). Foodstuffs which can be enriched according to the present invention with one or more compounds of the formula I are, for example, also foodstuffs which originate from a single natural source, such as, for example, sugars, unsweetened juice, nectar or puree from a single plant species, such as, for example, unsweetened apple juice (e.g. also a mixture of different types of apple juice), grapefruit juice, orange juice, stewed apples, apricot nectar, tomato juice, tomato sauce, tomato puree, etc. Further examples of foodstuffs which can be enriched according to the present invention with one or more compounds of the formula I are corn or cereals of a single plant species and materials which are prepared from such plant species, such as, for example, cereal syrup, rye flour, wheatmeal or oat bran. Mixtures of such foodstuffs are also suitable for being enriched according to the present invention with one or more compounds of the formula I, for example multivitamin preparations, mineral substance mixtures or sugared juice. Further examples which may be mentioned of foodstuffs which can be enriched according to the present invention with one or more compounds of the formula I are foodstuff preparations, for example prepared cereals, bakery products, mixed drinks, foodstuffs prepared specifically for children, such as yoghurt, diet foodstuffs, low-calorie foodstuffs or animal feed.

The foodstuffs which can be enriched according to the present invention with one or more compounds of the formula I thus include all palatable combinations of carbohydrates, lipids, proteins, inorganic elements, trace elements, vitamins, water or active metabolytes of plants and animals.

The foodstuffs which can be enriched according to the present invention with one or more compounds of the formula I are preferably used orally, e.g. in the form of foods, pills, tablets, capsules, powders, syrup, solutions or suspensions.

The foodstuffs according to the invention enriched with one or more compounds of the formula I can be prepared by techniques which are well known to the person skilled in the art.

As a result of their advantageous action, in particular as antioxidants or as free-radical scavengers, compounds of the formula I are also suitable as medicaments. In this connection, they have a supporting or substituting action for natural mechanisms which scavenge free radicals within the body. With regard to their activity, the compounds of the formula I may sometimes be compared with free-radical scavengers such as vitamin C. Compounds of the formula I can be used, for example, for the preventative treatment of inflammation and allergies of the skin, and in certain cases for preventing certain types of cancer.

Because of their antiallergic, antiinflammatory and anti-irritative effects, compounds of the formula I are suitable in particular for the preparation of a medicament for the treatment of inflammations, allergies and irritations, in particular of the skin.

In addition, it is possible to prepare medicaments which act as vein tonics, as agents for increasing the strength of blood capillaries, as inhibitants for cuperose, as inhibitors of chemical, physical or actinic erythemas, as agents for treating sensitive skin, as decongestants, as dehydrating agents, as weight-loss agents, as antiwrinkle agents, as stimulators of the synthesis of components of the extracellular matrix, as strengthening agents for improving elasticity of the skin and as anti-ageing agents.

A further subject-matter of the invention relates to the stabilization of UV filters. A known and high-performance class of light protection filter substances is formed by the dibenzoylmethane derivatives. However, a disadvantage is that these substances are very readily decomposed by UV light and thus lose their protective properties. One example which may be mentioned of a commercially available light protection filter from this class of compound is 4-(tert-butyl)-4'-methoxydibenzoylmethane, which has the structure shown below.

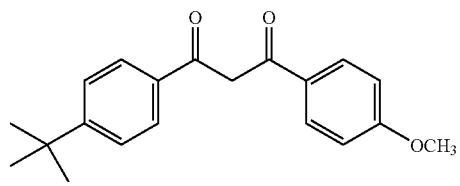

Surprisingly, it has now been found that compounds with the formula I have a very good stabilizing action for the dibenzoylmethanes, in particular 4-(tert-butyl)$_4$-methoxybenzoylmethane. A particularly high stabilizing action has been found for a compound of the formula I where X=—CH$_2$- and R$^1$=R$^2$=R$^3$=R$^4$=H. By incorporating mixtures of these compounds into cosmetics, it is now possible to prepare light protection compositions using dibenzoylmethanes which, even when subjected to prolonged periods of solar irradiation, for example during sunbathing for a number of hours, have no or only a very low reduction in the protective action against UV rays.

The invention is illustrated in more detail using examples.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

The entire disclosures of all applications, patents and publications, cited above or below, and of corresponding German patent application No. 10056400.3, filed Nov. 14, 2000, are hereby incorporated by reference.

EXAMPLES

Example 1

Introduction of a Protective Group on Quercetin:

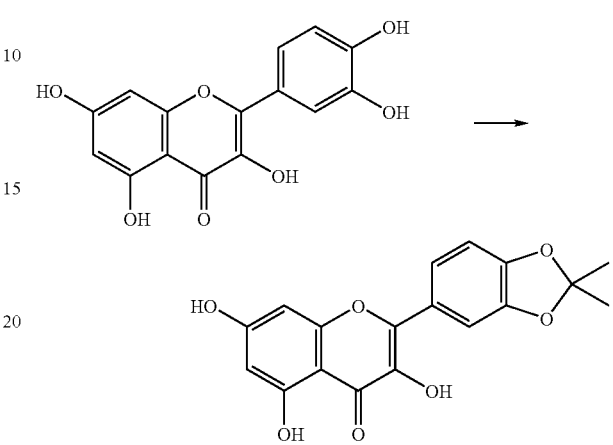

A mixture of quercetin (604 mg, 2 mmol) and diphosphorus pentoxide (284 mg) in dichloromethane (10 ml) is heated to 75° C. Acetone (0.3 ml) is added dropwise to the suspension, and the mixture is stirred for a further hour at 75° C. Following removal of an oily residue, NaOH (25%, 1.5 ml) is added to the reaction mixture. The isolated organic phase is then washed with water and obtained by removal of the solvent under reduced pressure.

Example 2

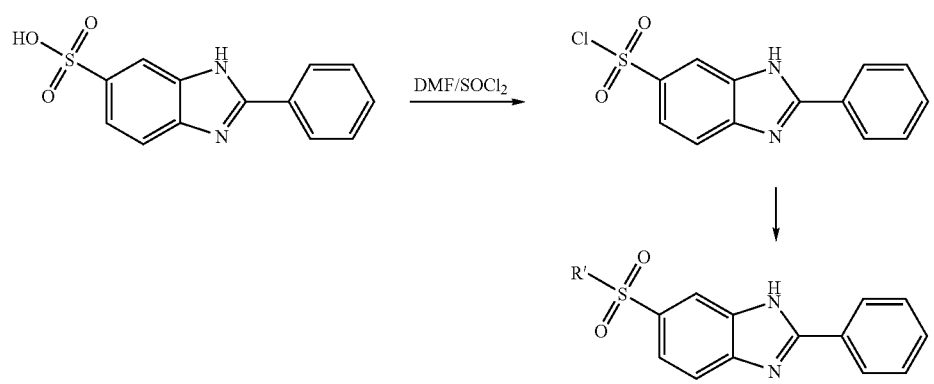

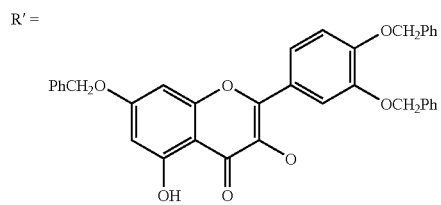

a) Chlorination of 2-phenylbenzimidazole-5-sulphonic Acid:

Dimethylformamide Chloride Synthesis:

Equimolar amounts of thionyl chloride and DMFA are mixed with cooling. The mixture is left to stand for 30 min at room temperature and is then evaporated to constant weight at 30-40° C. with the exclusion of moisture in a water-jet vacuum. This gives a pale yellow-coloured crystal sludge which is washed with ether.

Dimethylformamide chloride with 2-phenylbenzimidazole-5-sulphonic acid: 6.2 g of dimethylformamide chloride and 5 g of 2-phenylbenzimidazole-5-sulphonic acid are reacted in 120 ml of DMFA at 20° C. for 24 h. Ice is added to the mixture, which is then extracted with toluene. Following removal of the solvent, the desired product is obtained by recrystallization from $CH_2Cl_2$/hexane.

b) Reaction of 2-phenylbenzimidazole-5-sulphonyl Chloride with Acetone-protected Quercetin:

2-phenylbenzimidazole-5-sulphonyl chloride (2 mol) and 3',4',7-tribenzylquercetin (1 mol) are refluxed in toluene. The organic phase is then washed with an aqueous solution of potassium carbonate. Following separation of the organic phase, the desired product is obtained by removing the solvent under reduced pressure.

Example 3

Synthesis of 2-ethylhexyl 4-(dimethylamino)benzoate

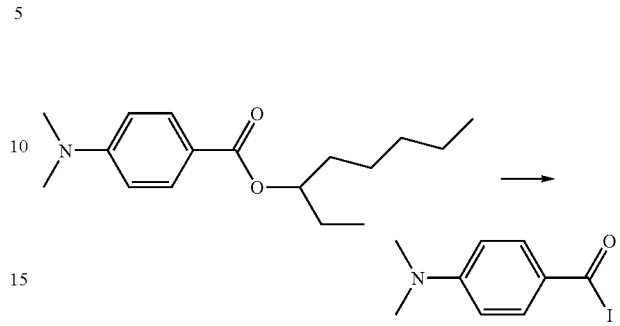

Iodine (0.1 mol) and diiodosilane (0.1 mol) are added to a solution of 2-ethylhexyl 4-(dimethylamino)benzoate (0.1 mol) in chloroform (5 ml). The reaction mixture is then stirred at 50° C. for 1.5 hours. Removal of the solvent gives 4-(dimethylamino)-2-acyliodide-benzene.

Example 4

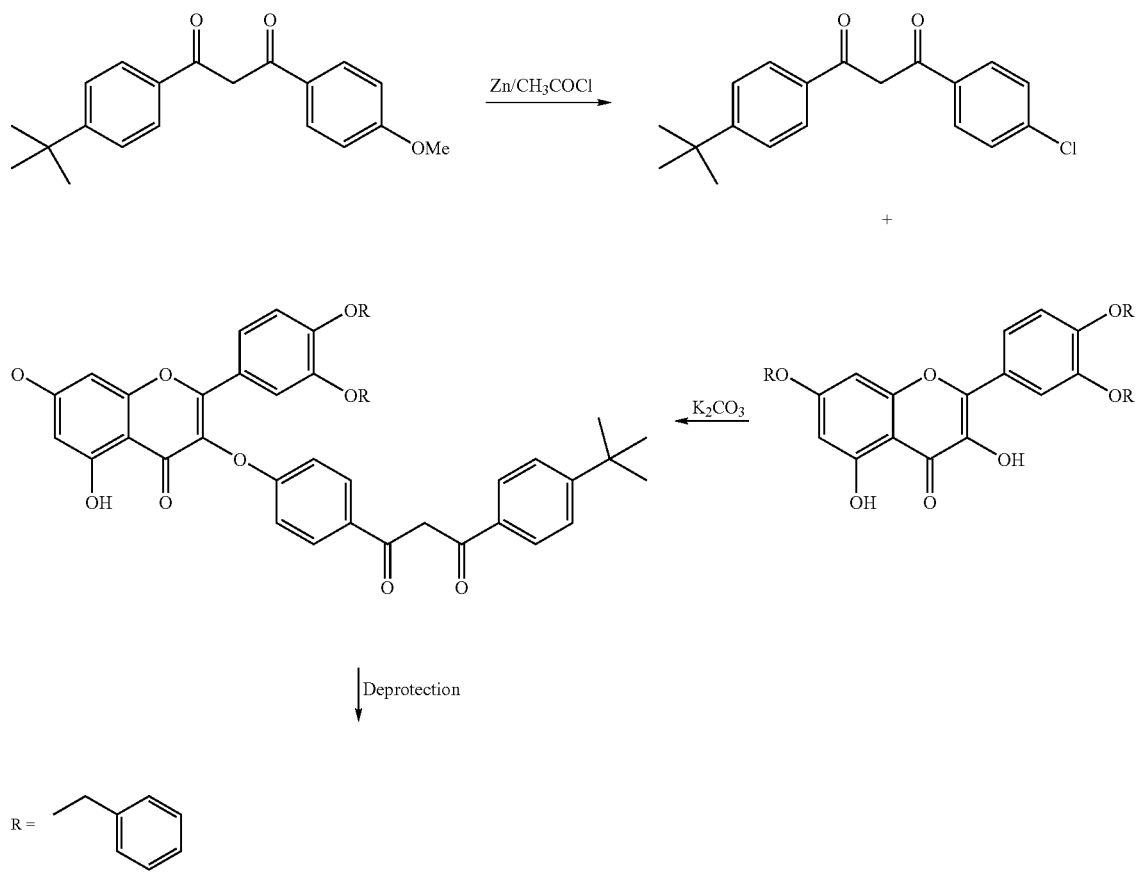

a) Chlorination of 1-(4-tert-butylphenyl)-3-(4-methoxyphenyl)propane-1,3-dione (Eusolex 9020)

1-(4-tert-butylphenyl)-3-(4-methoxyphenyl)propane-1,3-dione (2.48 g) and acetyl chloride are added to a suspension of zinc (130 mg) in ether (20 ml) under protective gas, and the mixture is stirred for a further 1.5 hours. The reaction mixture is then quenched with water. After solid zinc has been removed by means of filtration, the reaction mixture is washed with ether (5×5 ml). The combined organic phases are washed with sodium carbonate and sodium chloride solution and dried under reduced pressure.

b) Synthesis of the Ether:

A mixture of 3',4',7-tribenzylquercetin (3 g), 1-(4-tert-butylphenyl)-3-(4-chlorophenyl)propane-1,3-dione and $K_2CO_3$ (30 g) is refluxed in dried acetone (300 ml) for 21 hours. The solution is then suction-filtered, and washing is carried out a number times with warm acetone. The acetone is removed from the filtrate under reduced pressure to give the desired product.

c) Deprotection:

3',4',7-tribenzyl-2-(1-(4-tert-butylphenyl)-3-(4-oxophenyl)propane-1,3-dione)quercetin is dissolved in 200 ml of methanol and hydrogenated using 0.3 g of 10% Pd/carbon at 1 bar. Removal of the catalyst and of the solvent used gives the desired product.

Example 5

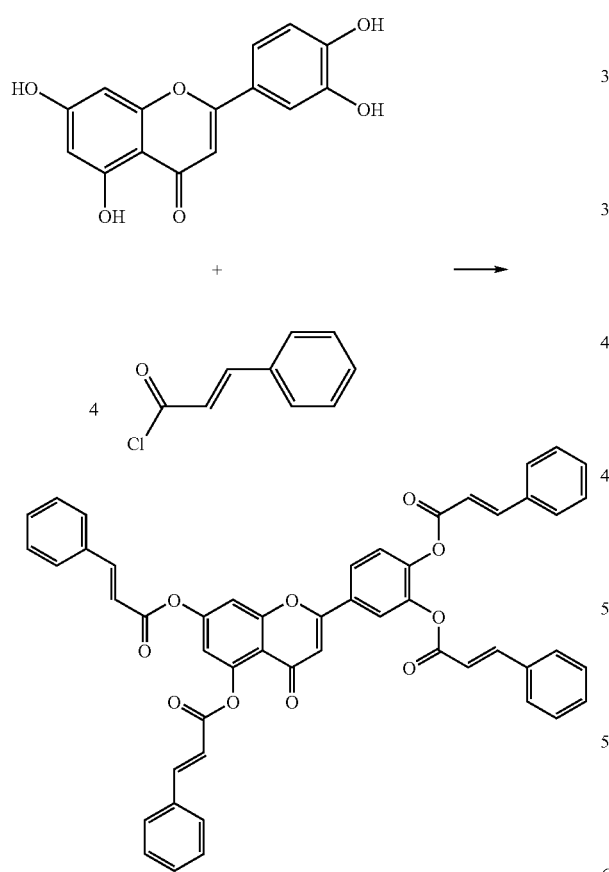

1 g of luteolin was introduced into 50 ml of pyridine and 50 ml of $CH_2Cl_2$, and, at room temperature, 100 ml of cinnamyl chloride, dissolved in 25 ml of $CH_2Cl_2$, were slowly added dropwise. When the addition was complete, the mixture was stirred for a further 3 hours at room temperature. 100 ml of $H_2O$ and 50 ml of $CH_2Cl_2$ were then added, the organic phase was separated off and the aqueous phase was extracted with $CH_2Cl_2$. The combined organic phases were washed with water, 2N hydrochloric acid and aqueous sodium carbonate solution, and then dried. Following distillation of the solvent and recrystallization from toluene, fine white crystals were obtained.

Yield: 2.16 g (83% of theory)

Example 6

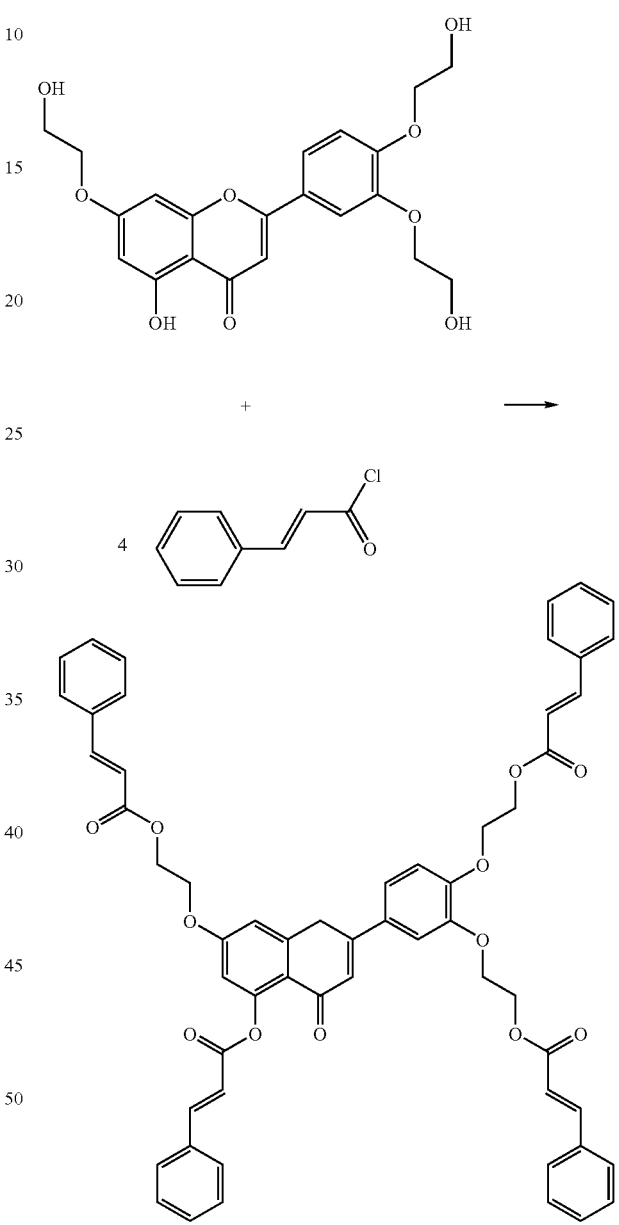

1 g of troxeluteolin and 50 ml of pyridine were introduced into 70 ml of $CH_2Cl_2$. A solution of 10 ml of cinnamyl chloride in 50 ml of $CH_2Cl_2$ was then slowly added dropwise at room temperature. When the addition was complete, the reaction mixture was stirred for a further 3 hours. 50 ml of water were added, and the organic phase was separated off and washed with water, 2N hydrochloric acid and again with water and then aqueous calcium carbonate solution. The organic phase was dried and then the solvent was distilled off under reduced pressure. Recrystallization from toluene gave a pale beige powder.

Yield: 1.09 g (67.3% of theory).

Example 7

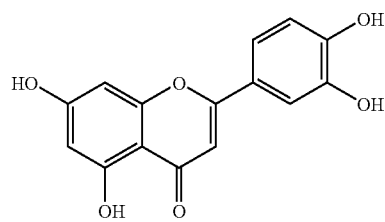

+

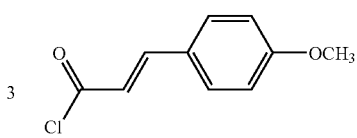

→

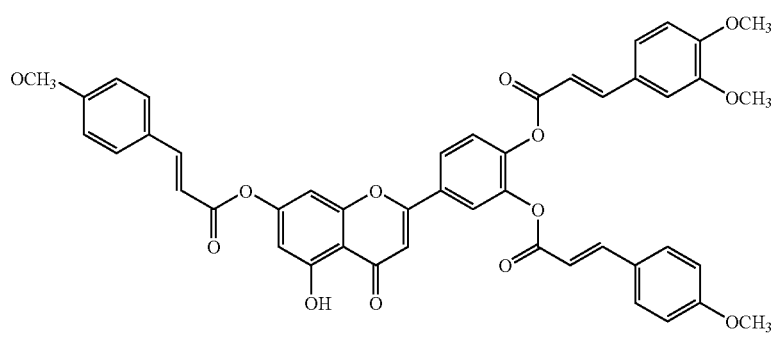

0.5 g of luteolin and 50 ml of pyridine were introduced into 25 ml of CH$_2$Cl$_2$, and 1.026 g of trans-p-methoxycinnamyl chloride in 25 ml of CH$_2$Cl$_2$ was slowly added dropwise at room temperature. When the addition was complete, the reaction mixture was stirred for a further 8 hours. 100 ml of water and 200 ml of CH$_2$Cl$_2$ were added, the organic phase was separated off and the aqueous phase was extracted with CH$_2$Cl$_2$. The combined organic phases were washed with water, 2N hydrochloric acid and saturated sodium chloride solution.

The solvent was distilled off under reduced pressure. Recrystallization from toluene gave a pale yellow powder.

Yield: 0.48 g (39% of theory).

Example 8

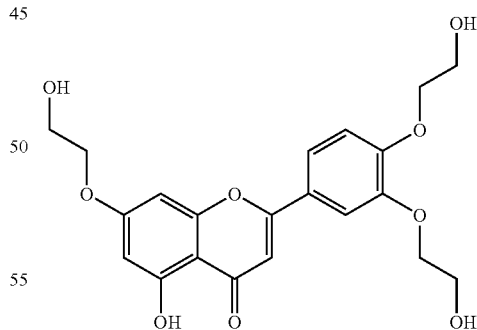

+

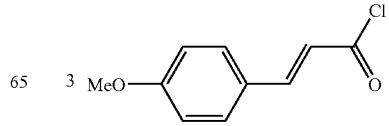

→

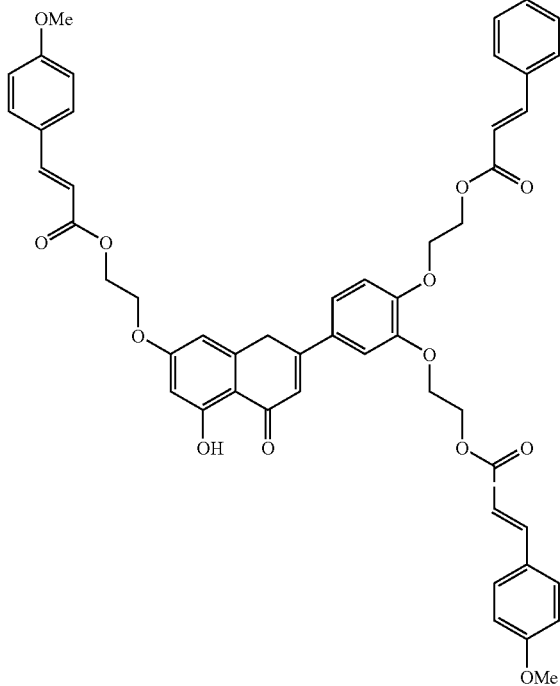

0.5 g of troxeluteolin and 25 ml of pyridine were introduced into 20 ml of $CH_2Cl_2$ and then 0.9838 g of trans-methoxycinnamyl chloride in 20 ml of $CH_2Cl_2$ were slowly added dropwise at room temperature. When addition was complete, the mixture was stirred for a further 8 hours. 100 ml of $H_2O$ and 50 ml of $CH_2Cl_2$ were added, the organic phase was separated off and the aqueous phase was extracted with $CH_2Cl_2$. The combined organic phases were washed with water, 2N hydrochloric acid and again with water. Following drying, the solvent was distilled off under reduced pressure. Recrystallization from toluene gave a pale yellow powder.

Yield: 0.63 g (59% of theory).

Exemplary compositions of cosmetic formulations are given below.

The compounds prepared in Examples 2 and 7 are used for the preparation of the compositions. Here, "compound 2" means the compound prepared in Example 2 and "compound 7" means the compound prepared in Example 7.

Example 1

| Care lotion (W/O) for application to the skin | % by wt |
| --- | --- |
| A Compound 7 | 1.00 |
| Polyglyceryl-2 dipolyhydroxystearate | 5.00 |
| Beeswax | 0.50 |
| Zinc stearate | 0.50 |
| Hexyl laurate | 9.00 |
| Cetyl isononanoate | 6.00 |
| Shea butter | 0.50 |
| DL-α-Tocopherol acetate | 1.00 |
| B Glycerol | 5.00 |
| Magnesium sulphate heptahydrate | 1.00 |
| Preservative | q.s. |
| Water, demineralized ad | 100.00 |

Preparation:

Phase A is heated to 75° C. and phase B is heated to 80° C. With stirring, phase B is slowly added to phase A. Following homogenization, the mixture is cooled with stirring. At a temperature of 40° C., perfume substances are added.

The preservatives used are:
0.05% of propyl 4-hydroxybenzoate
0.15% of methyl 4-hydroxybenzoate Example 2

| Care lotion (W/O) for application to the skin | % by wt |
| --- | --- |
| A Polyglyceryl-2 dipolyhydroxystearate | 5.00 |
| Beeswax | 0.50 |
| Zinc stearate | 0.50 |
| Hexyl laurate | 9.00 |
| Cetyl isononanoate | 6.00 |
| Shea butter | 0.50 |
| DL-α-Tocopherol acetate | 1.00 |
| B Compound 2 | 1.00 |
| Glycerol | 5.00 |
| Magnesium sulphate heptahydrate | 1.00 |
| Preservative | q.s. |
| Water, demineralized ad | 100.00 |

Preparation:

Phase A is heated to 75° C. and phase B is heated to 80° C. With stirring, phase B is slowly added to phase A. Following homogenization, the mixture is cooled with stirring. At a temperature of 40° C., perfume substances are added.

The preservatives used are:
0.05% of propyl 4-hydroxybenzoate
0.15% of methyl 4-hydroxybenzoate Example 3

| Skin cream (O/W) | % by wt |
| --- | --- |
| A Paraffin | 2.00 |
| Isohexadecane | 2.00 |
| Isopropyl palmitate | 3.00 |
| Soya oil | 0.50 |
| Dimethicone | 1.00 |
| Cetyl alcohol | 1.00 |
| Sorbitol stearate | 1.50 |
| Cetyl alcohol (and) cetyl glucoside | 4.00 |
| (−)-α-Bisabolol | 0.30 |
| B Water, demineralized ad | 100.00 |
| Compound 2 | 1.00 |
| Glycerol 87% | 10.00 |
| D-Panthenol | 0.50 |
| (D+)-Biotin | 0.05 |
| Preservative | q.s. |
| C Xanthan gum | 0.30 |
| D Perfume | 0.20 |

Preparation:

Phase A and phase B are heated separately to 75° C. Phase C is then slowly added to phase B and stirred until homogenized. The resulting B/C mixture is added to phase A at a temperature of 75° C., and the mixture is homogenized. Perfume substances are added after cooling to 35° C.

The preservatives used are:

0.05% of propyl 4-hydroxybenzoate 0.15% of methyl 4-hydroxybenzoate 0.30% of Germall 115 (ISP, Frechen)

Example 4

|   | % by wt |
|---|---|
| A Compound 7 | 1.00 |
| Paraffin | 2.00 |
| Isohexadecane | 2.00 |
| Isopropyl palmitate | 3.00 |
| Soya oil | 0.50 |
| Dimethicone | 1.00 |
| Cetyl alcohol | 1.00 |
| Sorbitol stearate | 1.50 |
| Cetyl alcohol (and) cetyl glucoside | 4.00 |
| (−)-α-Bisabolol | 0.30 |
| B Water, demineralized ad | 100.00 |
| Glycerol 87% | 10.00 |
| D-Panthenol | 0.50 |
| (D+)-Biotin | 0.05 |
| Preservative | q.s. |
| C Xanthan gum | 0.30 |
| D Perfume | 0.20 |

Preparation:

Phase A and phase B are heated separately to 75° C. Phase C is then slowly added to phase B and stirred until homogenized. The resulting B/C mixture is added to phase A at a temperature of 75° C. and the mixture is homogenized. After cooling to 35° C., perfume substances are added.

The preservatives used are:

0.05% of propyl 4-hydroxybenzoate 0.15% of methyl 4-hydroxybenzoate 0.30% of Germall 115 (ISP, Frechen)

Example 5

| Sunscreen spray (O/W) | % by wt |
|---|---|
| A Compound 7 | 1.00 |
| Eusolex ® 2292 (Art. No. 105382) | 7.50 |
| Eusolex ® HMS (Art. No. 111412) | 7.00 |
| Steareth-2 | 0.40 |
| Steareth-10 | 0.80 |
| Pemulen ® TR-2 | 1.18 |
| Propylene glycol isoceteth-3 acetate | 5.00 |
| Performa ® V 825 | 0.80 |
| Dimethicone | 1.00 |
| Oxynex ® K (Art. No. 108324) | 0.10 |
| B Eusolex ® 232 (Art. No. 105372) | 1.00 |
| Triethanolamine | 0.90 |
| 1,2-propanediol | 2.00 |

| Sunscreen spray (O/W) | % by wt |
|---|---|
| Preservative | 0.50 |
| Water, demineralized ad | 100.00 |

Eusolex ® 2292, Eusolex ® HMS and Eusolex ® 232 are UV filters which are sold by Merck KGaA, Darmstadt.
Pemulen ® TR-2 is an acrylate alkyl acrylate polymer which is sold by Goodrich, Neuss,
Performa ® V 825 is a synthetic wax which is sold by New Phase, NJ08554,
Oxynex ® K is a mixture of PEG-8, tocopherol, ascorbyl palmitate, ascorbic acid and citric acid and is sold by Merck KGaA, Darmstadt.

Preparation:

Phase B:

The water is mixed with the triethanolamine and then Eusolex® 232 is added with stirring. As soon as everything has dissolved, the further constituents of phase B are added and then the mixture is heated to 80° C.

Phase A:

The constituents of phase A, with the exception of Pemulen® TR-2, are combined and heated to 80° C. The Pemulen® TR-2 is then added with stirring.

Preparation of the Sunscreen Composition:

Phase B is slowly added with stirring to phase A. Following homogenization, the mixture is cooled with stirring.

The preservatives used were:

0.05% of propyl 4-hydroxybenzoate 0.15% of methyl 4-hydroxybenzoate

Example 6

| Sunscreen spray (O/W) | % by wt |
|---|---|
| A Eusolex ® 2292 (Art. No. 105382) | 7.50 |
| Eusolex ® HMS (Art. No. 111412) | 7.00 |
| Steareth-2 | 0.40 |
| Steareth-10 | 0.80 |
| Pemulen ® TR-2 | 0.18 |
| Propylene glycol isoceteth-3 acetate | 5.00 |
| Performa ® V 825 | 0.80 |
| Dimethicone | 1.00 |
| Oxynex ® K (Art. No. 108324) | 0.10 |
| B Compound 2 | 1.00 |
| Eusolex ® 232 (Art. No. 105372) | 1.00 |
| Triethanolamine | 0.90 |
| 1,2-propanediol | 2.00 |
| Water, demineralized ad | 100.00 |

Preparation:

Phase B:

The water is mixed with the triethanolamine and then Eusolex® 232 is added with stirring. As soon as everything has dissolved, the further constituents of phase B are added and then the mixture is heated to 80° C.

Phase A:

The constituents of phase A, with the exception of Pemulen® TR-2, are combined and heated to 80° C. The Pemulen® TR-2 is then added with stirring.

Preparation of the Sunscreen Composition:

Phase B is slowly added to phase A with stirring. Following homogenization, the mixture is cooled with stirring.

The preservatives used are:
0.05% of propyl 4-hydroxybenzoate
0.15% of methyl 4-hyrdoxybenzoate

Example 7

| Sunscreen gel (aqueous) | % by wt |
|---|---|
| A Compound 7 | 1.00 |
| Eusolex® 232 (Art. No. 105372) | 4.00 |
| Sodium hydroxide solution | 6.00 |
| Glycerol | 3.00 |
| 1,2-propanediol | 2.00 |
| Preservative | q.s. |
| Water, demineralized ad | 100.00 |
| B Carbomer Ultrez-10 | 0.70 |
| Water, demineralized | 60.00 |
| C Sodium hydroxide solution (10%) | 1.50 |
| Water, demineralized | 4.00 |

Carbomer Ultrez-10 is supplied by Goodrich, Neuss, Germany.

Preparation:

Carbomer Ultrez-10 is completely dispersed in the water of phase B. Phase C is then slowly added and homogenized.

For phase A, the water is firstly added to the sodium hydroxide solution and then the Eusolex® 232 is added and completely dissolved with stirring. After a clear solution has been obtained, the further constituents of phase A are added. Phase A is then added in portions to the mixture of phases B and C, the mixture being homogenized after each addition.

The preservative used is:
0.20% of methyl 4-hydroxybenzoate

Example 8

| Sunscreen gel (O/W) | % by wt |
|---|---|
| A Compound 7 | 1.00 |
| Eusolex® 6300 (Art. No. 5385) | 0.75 |
| Luvitol® EHO | 10.00 |
| Dimethicone | 2.00 |
| Shea butter | 5.00 |
| Antaron® V-220 | 2.00 |
| Oxynex® K | 1.00 |
| B Eusolex® 232 (Art. No. 5372) | 0.75 |
| Tris(hydroxymethyl)aminomethane | 0.33 |
| Preservative | q.s. |
| Water, demineralized | 20.00 |
| C Tris(hydroxymethyl)aminomethane | 1.20 |
| Water, demineralized | 10.00 |
| D Pemulen® TR-1 | 0.60 |
| Water, demineralized ad | 100.00 |

Pemulen® TR-1 is an acrylate/C_[lacuna]-C_[lacuna]-alkyl acrylate polymer which is sold by Goodrich, Neuss, Germany,
Eusolex® 6300 is a UV filter which is sold by Merck KGaA, Darmstadt, Germany,
Luvitol® EHO is sold by BASF AG, Ludwigshafen, Germany,
Antaron® V-220 is sold by GAF, Frechen, Germany.

Preparation:

The Pemulen® TR-1 is dissolved in the water of phase D. The tris(hydroxymethyl)aminomethane is dissolved in the water of phase C and the solution is added to phase D. The tris(hydroxymethyl)aminomethane is dissolved in the water of phase B and then the Eusolex® 232 is added with stirring. After an aqueous solution has been obtained, the further constituents of phase B are added and then phase B is added to the mixture of phases C and D and homogenized. The constituents of phase A are combined and heated. Phase A is then added to the mixture of the other phases with homogenization.

The preservatives used are:
0.05% of propyl 4-hydroxybenzoate
0.15% of methyl 4-hydroxybenzoate

Example 9

| Sunscreen gel (O/W) | % by wt |
|---|---|
| A Eusolex® 6300 (Art. No. 5385) | 0.75 |
| Luvitol® EHO | 10.00 |
| Dimethicone | 2.00 |
| Shea butter | 5.00 |
| Antaron® V-220 | 2.00 |
| Oxynex® K liquid (Art. No. 8324) | 1.00 |
| B Compound 2 | 1.00 |
| Eusolex® 232 (Art. No. 5372) | 0.75 |
| Tris(hydroxymethyl)aminomethane | 0.33 |
| Preservative | q.s. |
| Water, demineralized | 20.00 |
| C Tris(hydroxymethyl)aminomethane | 1.20 |
| Water, demineralized | 10.00 |
| D Pemulen® TR-1 | 0.60 |
| Water, demineralized ad | 100.00 |

Preparation:

The Pemulen® TR-1 is dissolved in the water of phase D. The tris(hydroxymethyl)aminomethane is dissolved in the water of phase C and the solution is added to phase D. The tris(hydroxymethyl)aminomethane is dissolved in the water of phase B and then the Eusolex® 232 is added with stirring. After a clear solution has been obtained, the further constituents of phase B are added and then phase B is added to the mixture of phases C and D and homogenized. The constituents of phase A are combined and heated. Phase A is then added to the mixture of the other phases with homogenization.

The preservatives used are:
0.05% of propyl 4-hydroxybenzoate
0.15% of methyl 4-hydroxybenzoate

Example 10

| Sunscreen lotion (W/O) with UVA/B protection | % by wt |
|---|---|
| A Compound 7 | 1.00 |
| Eusolex® 2292 (Art. No. 1.05382) | 3.00 |
| Eusolex® 4360 (Art. No. 1.05376) | 2.00 |
| Dehymuls® E | 6.00 |
| Hydrogenated castor oil | 1.00 |
| Beeswax | 2.00 |
| Oleyl erucate | 6.00 |
| Decyl oleate | 6.00 |
| Dicapryl ether | 5.00 |
| Dimethicone | 1.00 |
| B Glycerol (87%) | 5.00 |
| Magnesium sulphate heptahydrate | 1.00 |
| Preservative | q.s. |
| Water, demineralized ad | 100.00 |

Dehymuls® E is a mixture of dicocoyl pentaerythrityl citrate, sorbitol sesquioleate, beeswax and aluminium stearate and is sold by Henkel KGaA, Dusseldorf, Germany.

Preparation:

The constituents of phases A and B are mixed in each case. Phase A is heated to 75° C. and phase B is heated separately to 80° C. Phase B is added to phase A with homogenization. The mixture is then cooled with stirring.

The preservatives used are:
0.05% of propyl 4-hydroxybenzoate
0.15% of methyl 4-hydroxybenzoate Example 11

| Sunscreen lotion (W/O) with UVA/B protection | % by wt |
|---|---|
| A Eusolex ® 2292 (Art. No. 1.05382) | 3.00 |
| Eusolex ® 4360 (Art. No. 1.05376) | 2.00 |
| Dehymuls ® E | 6.00 |
| Hydrogenated castor oil | 1.00 |
| Beeswax | 2.00 |
| Oleyl erucate | 6.00 |
| Decyl oleate | 6.00 |
| Dicapryl ether | 5.00 |
| Dimethicone | 1.00 |
| B Compound 2 | 1.00 |
| Glycerol (87%) | 5.00 |
| Magnesium sulphate heptahydrate | 1.00 |
| Preservative | q.s. |
| Water, demineralized ad | 100.00 |

Preparation:

The constituents of phases A and B are mixed in each case. Phase A is heated to 75° C. and phase B is heated separately to 80° C. Phase B is added to phase A with homogenization. The mixture is then cooled with stirring.

The preservatives used are:
0.05% of propyl 4-hydroxybenzoate
0.15% of methyl 4-hydroxybenzoate The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A compound of the formula I where
X is O;
Y is O, S or NH;
a single or double bond may be provided between carbons C-2 and C-3;

$R^1$ and $R^2$, and $R^3$ and $R^4$ may be provided at any positions on the ring, and also $R^1$, $R^2$, $R^3$, $R^4$ and $R^5$ may be identical or different and independently of one another are —H, —OH or -OA; and A is a group which absorbs UV radiation selected from:

-continued

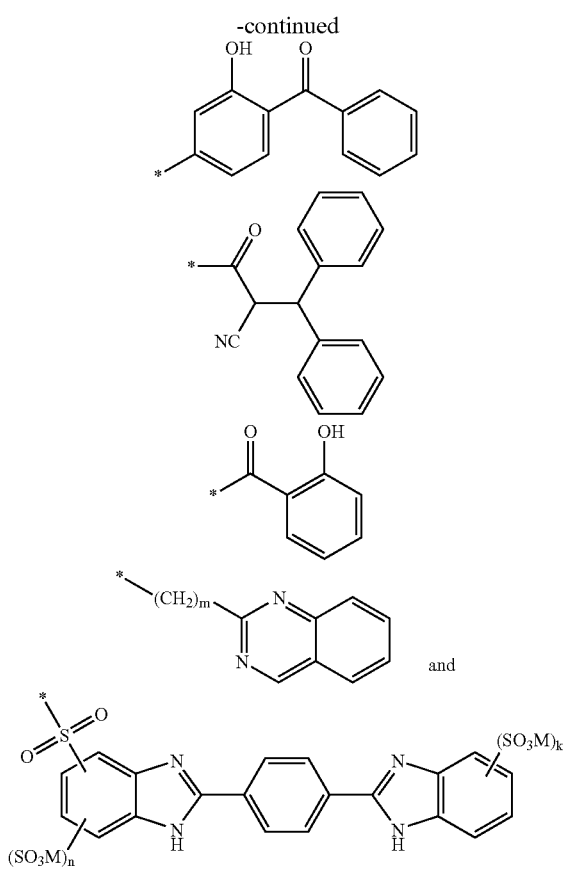

where
n is 0, 1, 2 or 3,
m is 0 or 1,
k is 0, 1, 2, 3 or 4, and
M is H, Na or K;
and at least one of $R^3$ and $R^4$ is other than H and at least one of the groups $R^1$, $1^2$, $R^3$, $R^4$ or $R^5$ is -OA.

2. A compound of formula I

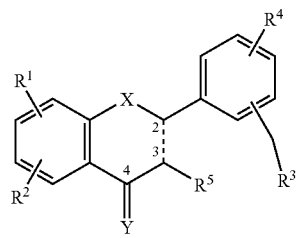

where
X is O;
Y is O, S or NH;
a single or double bond may be provided between carbons C-2 and C-3;
$R^1$ and $R^2$, and $R^3$ and $R^4$ may be provided at any positions on the ring, and also $R^1$, $R^2$, $R^3$, $R^4$ and $R^5$ may be identical or different and independently of one another are —H, —OH, -OA, a straight-chain or branched oxyalkyl or carboxyalkyl group having 1 to 12 carbon atoms, a straight-chain or branched oxyalk-enyl or carboxyalkenyl group having 2 to 12 carbon atoms, a straight-chain or branched hydroxyoxyalkyl group having 1 to 12 carbon atoms, where the hydroxyl group is bonded to a primary or secondary carbon atom and the alkyl chain is optionally interrupted by oxygen, a sulphate group, a phosphate group, or a mono- or oligoglycosyl radical; and A is a group which absorbs UV radiation selected from:

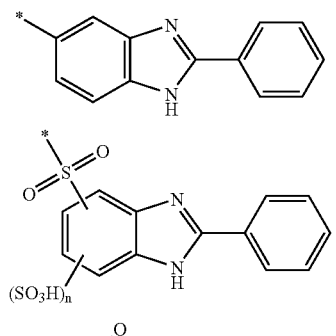

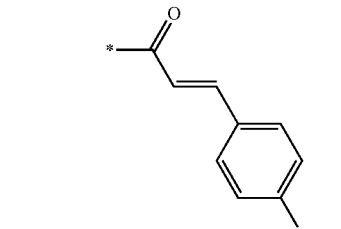

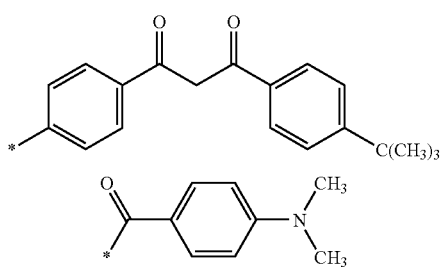

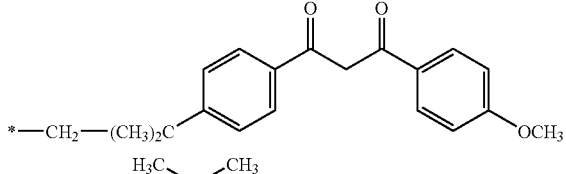

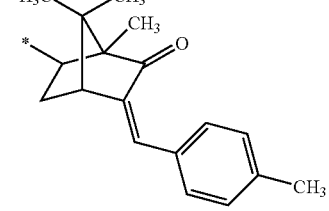

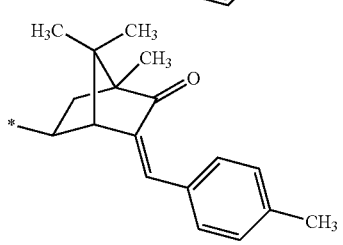

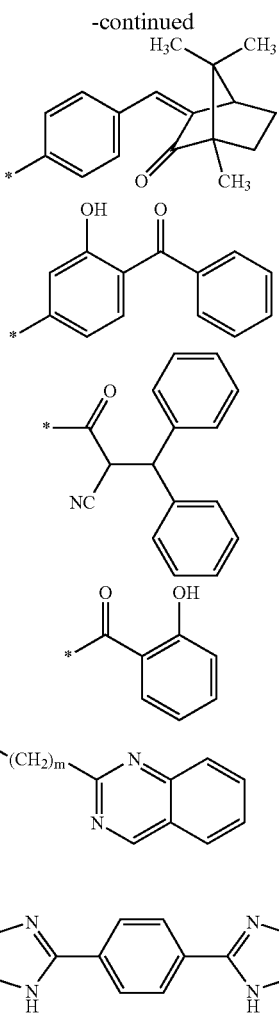

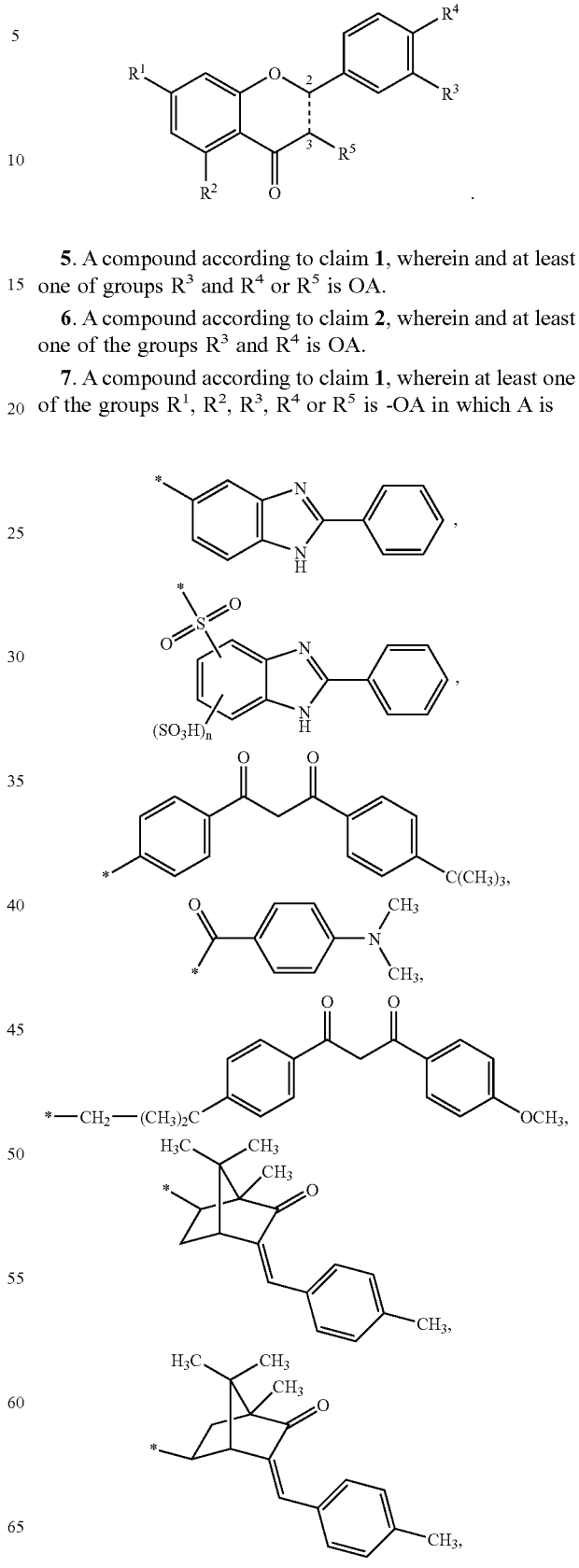

where n is 0, 1, 2 or 3, m is 0 or 1, k is 0, 1, 2, 3 or 4, and

M is H, Na or K;

and at least one of $R^3$ and $R^4$ is other than H and at least one of the groups $R^1$, $R^2$, $R^3$, $R^4$ or $R^5$ is -OA.

3. A compound according to claim 1, wherein said compound is of formula II

4. A compound according to claim 2, wherein said compound is of formula II

5. A compound according to claim 1, wherein and at least one of groups $R^3$ and $R^4$ or $R^5$ is OA.

6. A compound according to claim 2, wherein and at least one of the groups $R^3$ and $R^4$ is OA.

7. A compound according to claim 1, wherein at least one of the groups $R^1$, $R^2$, $R^3$, $R^4$ or $R^5$ is -OA in which A is -continued
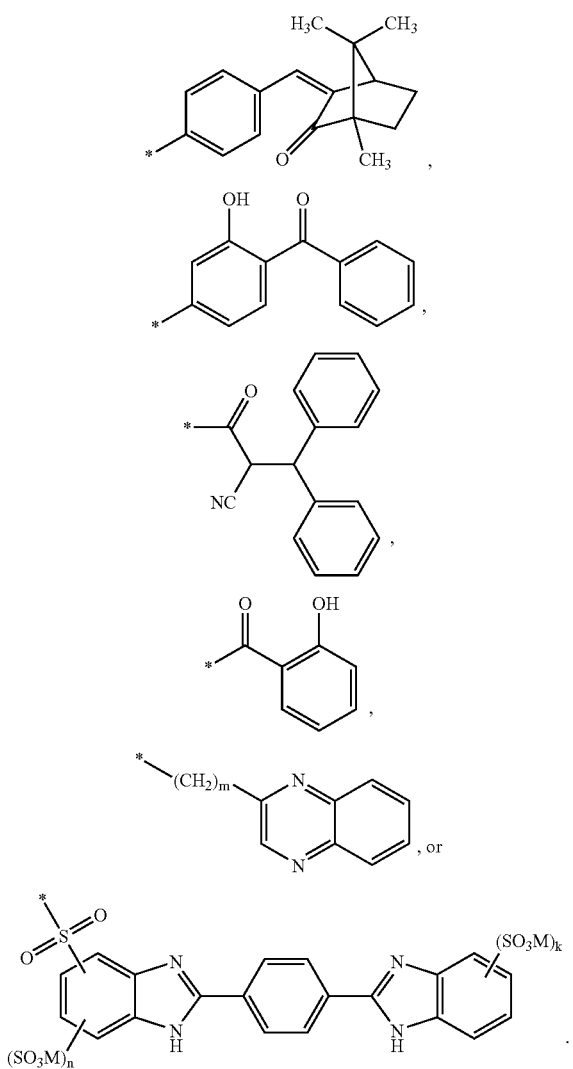
8. A compound according to claim 2, wherein at least one of the groups $R^1$, $R^2$, $R^3$, $R^4$ or $R^5$ is -OA in which A is
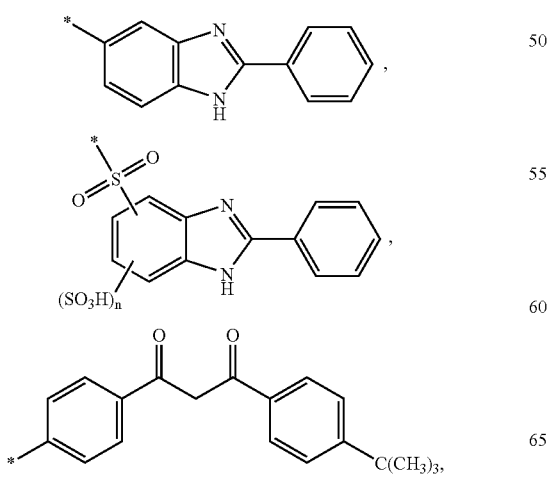
-continued
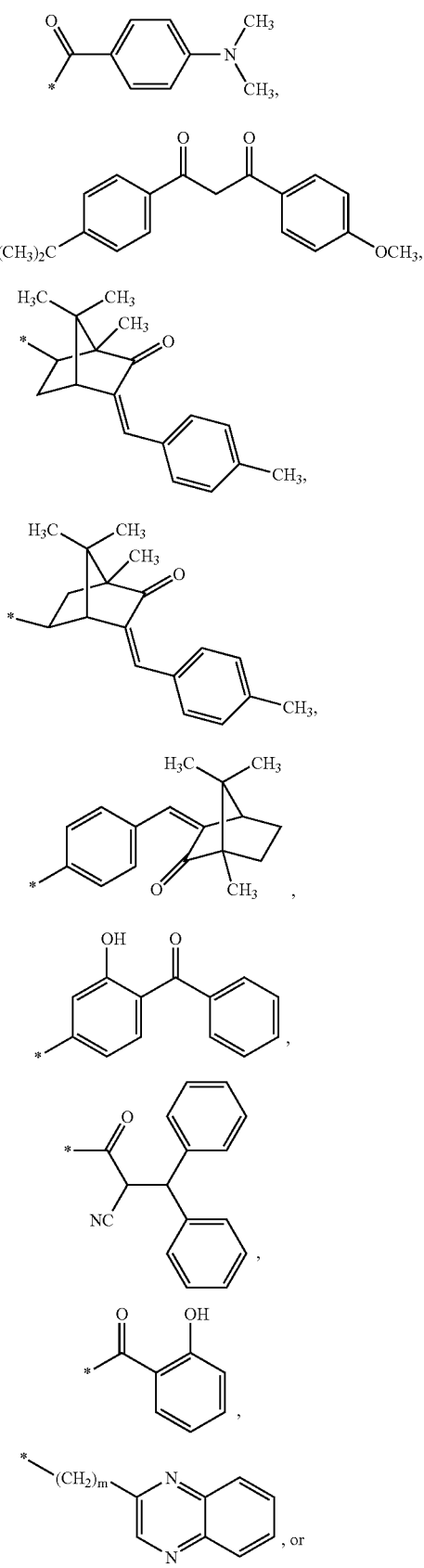

-continued

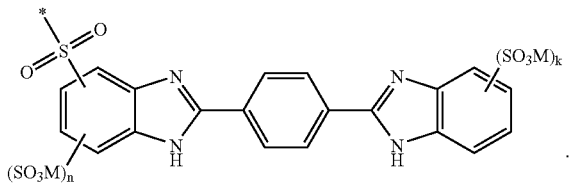

9. A compound according to claim 1, wherein and at least two of the groups $R^1$, $R^2$, $R^3$, $R^4$ or $R^5$ is OA.

10. A compound according to claim 1, wherein at least three of the groups $R^1$, $R^2$, $R^3$, $R^4$ or $R^5$ is OA.

11. A compound according to claim 1, wherein at least one of the groups $R^3$ and $R^4$ is OA.

12. A compound according to claim 1, wherein at least one of the groups $R^1$ and $R^2$ is OA.

13. A compound according to claim 1, wherein $R^5$ is H.

14. A compound according selected from the following compounds:

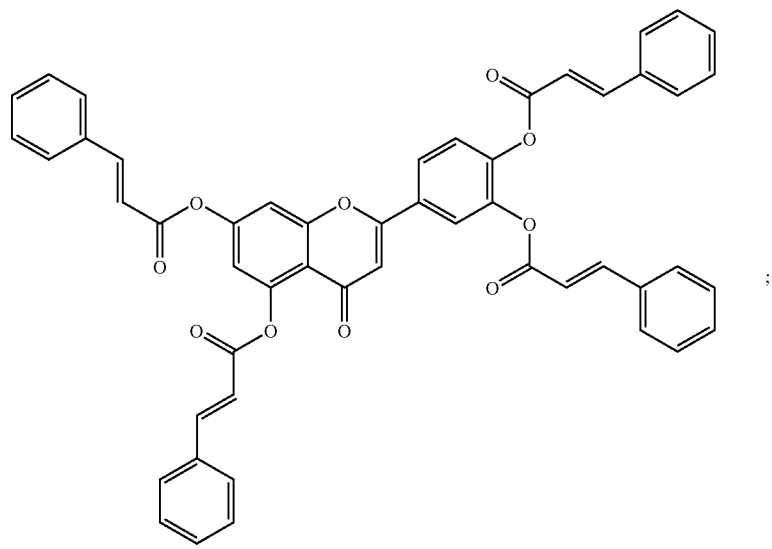

;

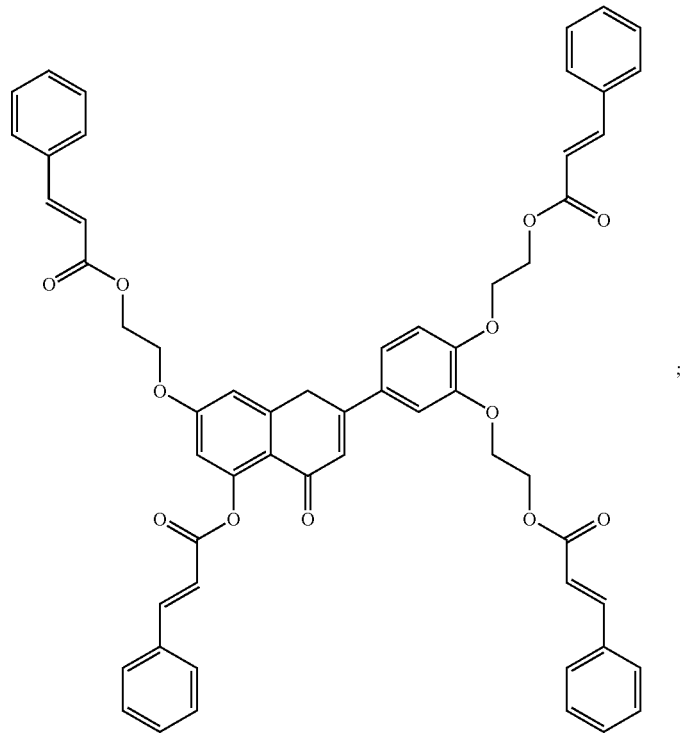

;

-continued

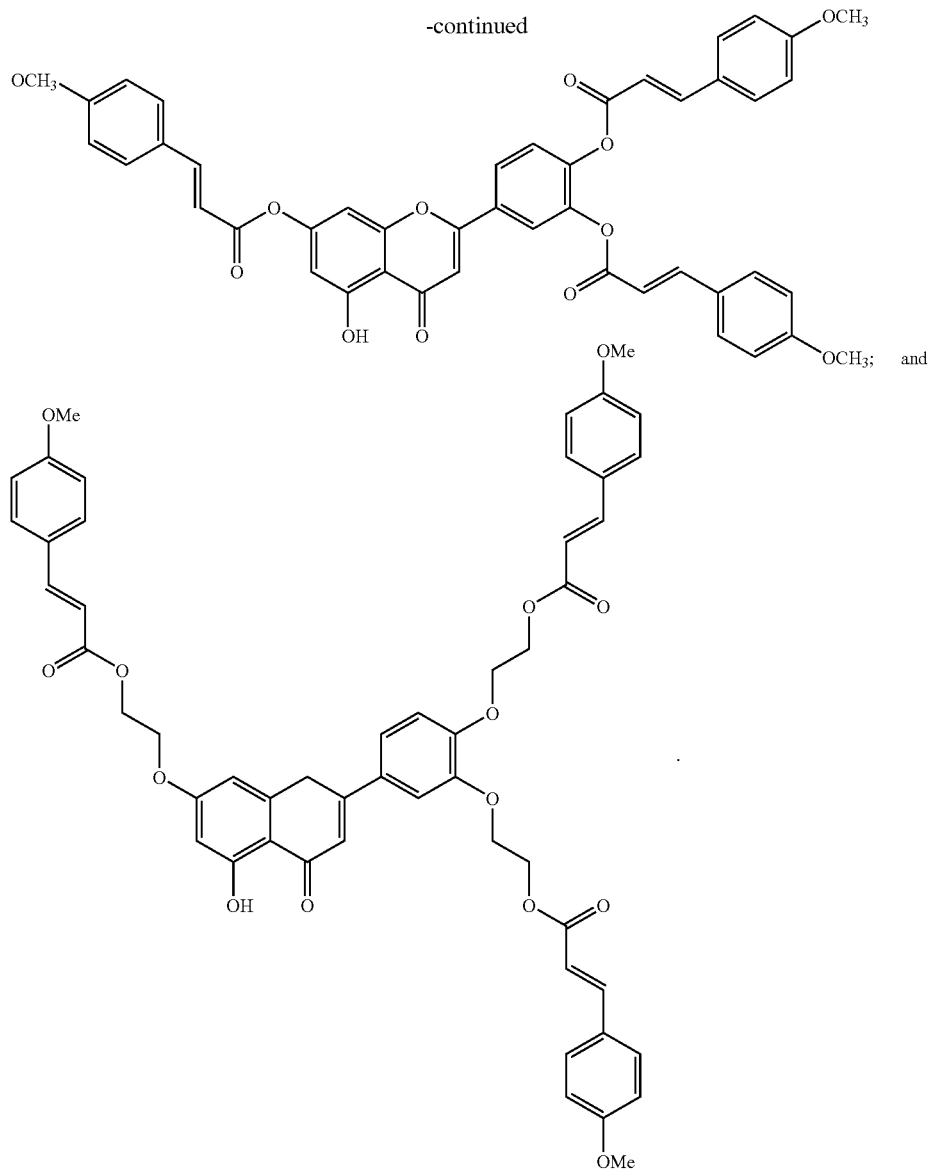

15. In a cosmetic or pharmaceutical formulation comprising an active ingredient and a physiologically acceptable carrier, the improvement wherein said formulation comprises at least one compound according to claim 1.

16. In a cosmetic or pharmaceutical formulation comprising an active ingredient and a physiologically acceptable carrier, the improvement wherein said formulation comprises at least one compound according to claim 2.

17. A cosmetic or pharmaceutical formulation according to claim 15, wherein said compound is of formula II

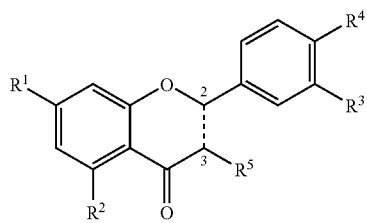

18. A cosmetic or pharmaceutical formulation according to claim 16 wherein said compound is of formula II

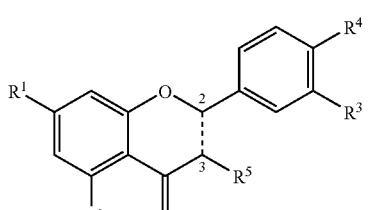

19. A cosmetic formulation according to claim 15, where the formulation comprises one or more additional UV filters and/or antioxidants.

20. A cosmetic formulation according to claim 16, where the formulation comprises one or more additional UV filters and/or antioxidants.

21. An enriched foodstuff comprising a foodstuff and at least one compound according to claim 1.

22. An enriched foodstuff comprising a foodstuff and at least one compound according to claim 2.

23. In a method of preparing a medicament comprising combining an active ingredient with a carrier, the improvement wherein said medicament contains an antioxidant effective amount of a compound according to claim 1.

24. In a method of preparing a medicament comprising combining an active ingredient with a carrier, the improvement wherein said medicament contains an antioxidant effective amount of a compound according to claim 2.

25. In a method of providing a cosmetic formulation with antioxidant properties, the improvement wherein a compound according to claim 2 is added to said cosmetic formulation as an antioxidant.

26. In a method of stabilizing a UV filter, the improvement wherein a compound according to claim 2 is used to stabilize the UV filter.

27. In a method of providing a cosmetic formulation with antioxidant properties, the improvement wherein a compound according to claim 1 is added to said cosmetic formulation as an antioxidant.

28. In a method of stabilizing a UV filter, the improvement wherein a compound according to claim 1, is used to stabilize the UV filter.

* * * * *

UNITED STATES PATENT AND TRADEMARK OFFICE
CERTIFICATE OF CORRECTION

PATENT NO.       : 7,345,090 B2  
APPLICATION NO. : 10/833137  
DATED            : March 18, 2008  
INVENTOR(S)      : Herwig Buchholz Page 1 of 1

It is certified that error appears in the above-identified patent and that said Letters Patent is hereby corrected as shown below:

Column 31, line 42 reads "ofthe groups $R^1$, $1^2$" should read --of the groups $R^1$, $R^2$--

Column 33, line 50 reads "ofthe groups" should read --of the groups--

Signed and Sealed this

Twenty-first Day of October, 2008

JON W. DUDAS  
*Director of the United States Patent and Trademark Office*